United States Patent [19]

Suzuki et al.

[11] Patent Number: 4,901,238

[45] Date of Patent: Feb. 13, 1990

[54] OXIMETER WITH MONITOR FOR DETECTING PROBE DISLODGEMENT

[75] Inventors: Susumu Suzuki; Sumio Yagi; Naotoshi Hakamata; Takeo Ozaki, Shizuoka, all of Japan

[73] Assignee: Hamamatsu Photonics Kabushiki Kaisha, Shizuoka, Japan

[21] Appl. No.: 188,912

[22] Filed: May 2, 1988

[30] Foreign Application Priority Data

May 8, 1987 [JP] Japan .................. 62-110461

[51] Int. Cl.⁴ .......................................... G06F 15/42
[52] U.S. Cl. ............................. 364/413.09; 128/633; 200/61.02
[58] Field of Search .................. 128/633, 664, 665; 356/40, 41, 51; 364/413.01, 413.09; 200/61.02

[56] References Cited

U.S. PATENT DOCUMENTS

| | | | |
|---|---|---|---|
| 3,893,767 | 7/1975 | Fulwyler et al. | 356/39 |
| 3,936,192 | 2/1976 | Skala | 356/104 |
| 4,223,680 | 9/1980 | Jobsis | 128/633 |
| 4,281,645 | 4/1983 | Jobsis | 128/633 |
| 4,294,263 | 10/1981 | Hochman | 128/736 |
| 4,295,475 | 10/1981 | Torzala | 128/736 |
| 4,321,930 | 3/1982 | Jobsis et al. | 128/633 |
| 4,331,161 | 5/1982 | Patel | 128/736 |
| 4,380,240 | 4/1983 | Jobsis et al. | 128/633 |
| 4,510,938 | 4/1985 | Jobsis et al. | 128/633 |
| 4,805,623 | 2/1989 | Jöbsis | 128/633 |

FOREIGN PATENT DOCUMENTS

| | | | |
|---|---|---|---|
| 0102816 | 3/1984 | European Pat. Off. | 128/633 |
| 2061496A | 5/1981 | United Kingdom . | |
| 2075668A | 11/1981 | United Kingdom . | |
| 2151020A | 7/1985 | United Kingdom . | |

OTHER PUBLICATIONS

Tamura, M. et al., "Measurement of Living Body Near Infrared Light Spectrophotometry", Near-Infrared Tissue Spectroscopy, vol. 23, No. 4, pp. 377–385, 1986, (in Japanese).

Wyatt, J. S. et al., "Quantification of Cerebral Oxygenation and Haemodynamics in Sick Newborn Infants by Near Infrared Spectrophotometry", The Lancet, pp. 1063–1066, Nov. 8, 1986.

Primary Examiner—Jerry Smith
Assistant Examiner—David Huntley
Attorney, Agent, or Firm—Finnegan, Henderson, Farabow, Garrett and Dunner

[57] ABSTRACT

An examination apparatus measures the oxygenation of body organs by using the near infrared transmission spectrophotometry. To assure the measurement reliability and the object person's safety, the examination apparatus monitors the variation of the fitting position of an illumination-side fixture by detecting the reflection light quantity from the measuring object.

6 Claims, 5 Drawing Sheets

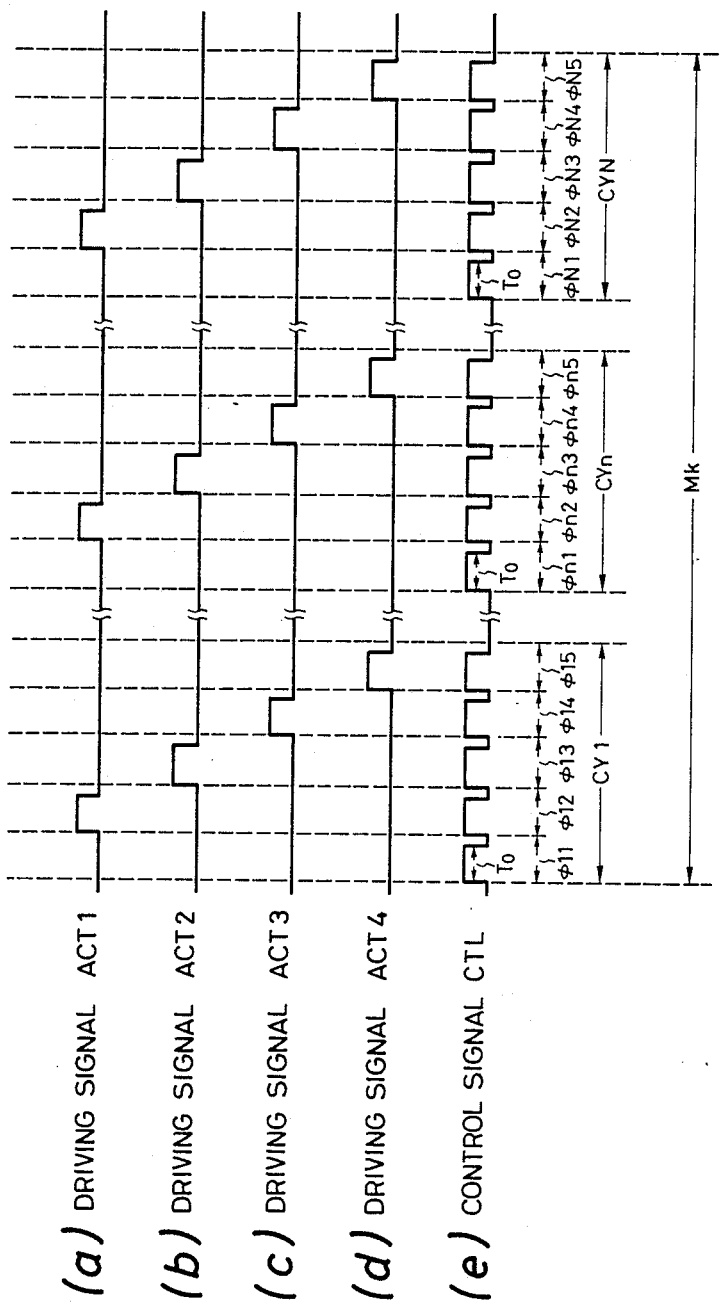

OXIMETER WITH MONITOR FOR DETECTING PROBE DISLODGEMENT

BACKGROUND OF THE INVENTION

The present invention relates to the apparatus for measuring the oxygen quantity in objects such as organs, e.g., the cerebral tissues of a human body or an animal. The invention especially relates to the apparatus for measuring the oxygenation of hemoglobin in blood and of cytochrome in cells by detecting those through electromagnetic waves.

In general, in diagnosing the function of a body organ, such as the cerebral tissues, the fundamental and important parameters to measure are the oxygen quantity in the body organ and the organ's utilization of oxygen. Supplying body organs with a sufficient quantity of oxygen is indispensable for the growth ability of fetuses and new-born infants. If the supply of oxygen to a fetus is insufficient, the probability that the fetus will not survive or that the new-born infant will die is high. Even if the newborn infant lives the serious problems in the body organs may remain as sequelae. The insufficiency of oxygen affects every body organ, but especially causes a serious damage in the cerebral tissues.

To examine the oxygen quantity in body organs readily and at the early stage of illness, an examination apparatus disclosed in U.S. Pat. No. 4,281,645 patented on Aug. 4, 1981 has been developed. In this kind of examination apparatus, the variation of oxygen quantity in body organs, especially in the brain, is measured through the absorption spectrum of near infrared light. The absorption is caused by the hemoglobin which is an oxygen-carrying medium in blood and the cytochrome a, $a_3$ which performs oxydation-reduction reaction in cells. As shown in FIG. 4(a), the absorption spectra of near infrared light (700 to 1300 nm), $\alpha_{HbO2}$ and $\alpha_{Hb}$ by oxygenated hemoglobin ($HbO_2$) and disoxygenated hemoglobin (Hb), respectively, are different from each other. And as shown in FIG. 4(b), the absorption spectra of $\alpha_{CyO2}$ and $\alpha_{Cy}$ by oxidized cytochrome a, $a_3$ ($CyO_2$) and reduced cytochrome a, $a_3$ (Cy), respectively, are different from each other. This examination apparatus utilizes the above-described absorption spectra of near infrared light. Four near infrared light rays with different wavelengths, $\lambda_1$, $\lambda_2$, $\lambda_3$ and $\lambda_4$ (e.g. 775 nm, 800 nm, 825 nm and 850 nm) are applied to one side of the patient's head with a time-sharing method and the transmission light rays from the opposite side of the head are in turn detected. By processing these four detected light rays with the prescribed calculation program the density variations of oxygenated hemoglobin ($HbO_2$), disoxygenated hemoglobin (Hb), oxidized cytochrome a, $a_3$ ($CyO_2$) and reduced cytochrome a, $a_3$ (Cy) are calculated. These parameters, in turn, determine the variation of cerebral oxygen quantity.

FIG. 5 shows a system outline of the above-described conventional examination apparatus 45. The conventional examination apparatus 45 includes; light sources such as laser diodes LD1 to LD4 which emit four near infrared light rays with different wavelengths of $\lambda_1$, $\lambda_2$, $\lambda_3$ and $\lambda_4$, respectively; a light source control device 55 which controls output timing of the light sources LD1 to LD4; optical fibers 50-1 to 50-4 which introduces near infrared light rays emitted by the light sources LD1 to LD4 to a patient's head 40; an illumination-side fixture 51 which bundles and holds end portions of the optical fibers 50-1 to 50-4; a detection-side fixture 52 which is fitted to the prescribed position of the opposite side of the patient's head 40; an optical fiber 53 which is held by the detection-side fixture 52 and introduces transmitted near infrared light from the patient's head 40; a transmission light detection device 54 which measures transmission quantity of near infrared light by counting photons of near infrared light introduced by the optical fiber 53; and a computer system 56 which controls the total examination apparatus and determines the variation of oxygen quantity in cerebral tissues being based on the transmission quantity of near infrared light.

The computer system 56 is equipped with a processor 62, a memory 63, output devices 64 such as a display and a printer, and an input device 65 such as a keyboard, and these devices are connected to each other by a system bus 66. The light source control device 55 and the transmission light detection device 54 are connected to the system bus 66 as external I/O's.

The light source control device 55 receives instructions from the computer system 56 and drives the light sources LD1 to LD4 by respective driving signals ACT1 to ACT4 as shown in FIGS. 6(a) to 6(d). As shown in FIG. 6 one measuring period $M_k$ ($k=1, 2, \ldots$) consists of N cycles of CY1 to CYn. At a phase $\phi n1$ in an arbitrary cycle CYn, no light source of LD1 to LD4 is driven and therefore the patient's head 40 is not illuminated by the near infrared light from the light sources LD1 to LD4. At the phase $\phi n2$ the light source LD1 is driven and the near infrared light with the wavelength of, for example, 775 nm is emitted from it. In the same manner, at the phase n3 the light source LD2 is driven and the near infrared light with the wavelength of, for example, 800 nm is emitted from it; at the phase $\phi n4$ the light source LD3 is driven and the near infrared light with the wavelength of, for example, 825 nm is emitted from it; and at the phase $\phi n5$ the light source LD4 is driven and the near infrared light with the wavelength of, for example, 850 nm is emitted from it. In this manner the light source control device 55 drives the light sources LD1 to LD4 sequentially with a time-sharing method.

Referring again to FIG. 5, the transmission light detection device 54 is equipped with a filter 57 which adjusts the quantity of near infrared light outputted to lenses 70 and 71 from the optical fiber 53; a photomultiplier tube 58 which converts the light from the filter 57 into pulse current and outputs it; an amplifier 59 which amplifies the pulse current from the photomultiplier tube 58; an amplitude discriminator 60 which eliminates the pulse current from the amplifier 59 whose amplitude is smaller than the prescribed threshold value; a multi-channel photon-counter 61 which detects photon frequency in every channel; a detection controller 67 which controls detection periods of the multi-channel photon-counter 61; and a temperature controller 68 which controls the temperature of a cooler 69 containing the photomultiplier tube 58.

To use the above-described examination apparatus, the illumination-side fixture and the detection-side fixture are firmly fitted to the prescribed positions of the patient's head 40 by using tape or the like. Once fitted, the light sources LD1 to LD4 are driven by the light source control device 55 as shown in FIGS. 6(a) to 6(d), respectively, so that the four near infrared light rays with different wavelengths are emited from the light sources LD1 to LD4 sequentially with the time-sharing method, and the light rays are introduced by the optical fibers 50-1 to 50-4 to the patient's head 40. As bones and soft tissues in the patient's head 40 are transparent to the near infrared light, the near infrared light is partially absorbed by hemoglobin in blood and cytochrome a, $a_3$ in cells and outputted to the optical fiber 53. The optical fiber 53 introduces the light to the transmission light detection device 54. At the phase $\phi n1$ no light source of LD1 to LD4 is driven, and therefore, the transmission light detection device 54 detects dark light.

The photomultiplier tube 58 in the transmission light detection device 54 is used with a photon-counting device that has high sensitivity and operates at high response speed. The output pulse current from the photomultiplier tube 58 is sent to the amplitude discriminator 60 through the amplifier 59. The amplitude discriminator 60 eliminates the noise component whose amplitude is smaller than the prescribed amplitude threshold and sends only the signal pulse to the multi-channel photon-counter 61. The multi-channel photon-counter 61 detects photons only in the periods $T_o$. The periods $T_o$ are synchronized with the driving signals ACT1 to ACT4 for the respective light sources LD1 to LD4 as shown in FIGS. 6(a) to (d) by a control signal CTL as shown in FIG. 6(e). The control signal CTL is generated by the detection controller 67. The multi-channel photon-counter then counts detected photon number of every light with each wavelength sent from the optical fiber 53. The transmission data of every near infrared light with each wavelength are obtained through the above-described procedure.

As shown in FIGS. 6(a) to (e), at the phase $\phi n1$ in the cycle CYn of light source control device 55 no light source of LD1 to LD4 is driven, therefore the dark light data d are counted by the transmission light detection device 54. At the phases $\phi n2$ to $\phi n5$ the light sources LD1 to LD4 are sequentially driven with the time-sharing method and the transmission light detection device 54 sequentially counts the transmission data $t_{\lambda 1}$, $t_{\lambda 2}$, $t_{\lambda 3}$ and $t_{\lambda 4}$ of the respective near infrared light rays with different wavelengths $\lambda_1$, $\lambda_2$, $\lambda_3$ and $\lambda_4$.

The counting of the dark light data d and the transmission data $t_{\lambda 1}$, $t_{\lambda 2}$, $t_{\lambda 3}$ and $t_{\lambda 4}$ which is sequentially performed in the cycle CYn, is continued N times from CY1 to CYn. That is, one measuring period $M_k$ (k=1, 2, ...) includes N cycles. A concrete example is as follows; if one cycle is 200 $\mu$sec and N is 10000, the measuring period $M_k$ becomes 2 sec. At the time of finishing of one measuring period $M_k$, the counting result of the dark light data D $$\left( = \sum_{n=1}^{N} d/CYn \right)$$

and the counting results of the transmission data $T_{\lambda 1}$, $T_{\lambda 2}$, $T_{\lambda 3}$ and $T_{\lambda 4}$ $$\left( = \sum_{n=1}^{N} t_{\lambda j}/CYn \right)$$

are transferred to the computer system 56 and stored in the memory 63.

The processor 62 performs the subtraction of the dark light component by using the combination of the transmission data and the dark data $(T_{\lambda 1}, T_{\lambda 2}, T_{\lambda 3}, T_{\lambda 4}, D)_{Mk}$ being stored in the memory 63 after one measuring period $M_k$ and the combination of those $(T_{\lambda 1}, T_{\lambda 2}, T_{\lambda 3}, T_{\lambda 4}, D)_{Mo}$ at the start of measuring, and calculates the variation rates of the transmission light $\Delta T_{\lambda 1}$, $\Delta T_{\lambda 2}$, $\Delta T_{\lambda 3}$ and $\Delta T_{\lambda 4}$. That is, the variation rates of the transmission light $\Delta T_{\lambda 1}$, $\Delta T_{\lambda 2}$, $\Delta T_{\lambda 3}$ and $\Delta T_{\lambda 4}$ are calculated as:

$$\Delta T_{\lambda j} = \log[(T_{\lambda j} - D)_{Mk}/(T_{\lambda j} - D)_{Mo}] (j=1 \text{ to } 4). \quad (1)$$

The use of logarithm in the above calculation of $\Delta T_{\lambda j}$ is to express the variation as an optical density.

Using the above-calculated variation rates of the transmission light $\Delta T_{\lambda 1}$, $\Delta T_{\lambda 2}$, $\Delta T_{\lambda 3}$ and $\Delta T_{\lambda 4}$, density variations of oxygenated hemoglobin ($HbO_2$), disoxygenated hemoglobin (Hb), oxidized cytochrome a, $a_3$ ($CyO_2$) and reduced cytochrome a, $a_3$ which are expressed as $\Delta X_{HbO2}$, $\Delta X_{Hb}$, $\Delta X_{CyO2}$ and $\Delta X_{Cy}$, respectively, can be determined. That is, each of density variations of $\Delta X_{HbO2}$, $\Delta X_{Hb}$, $\Delta X_{CyO2}$ and $\Delta X_{Cy}$ is calculated as:

$$\Delta X_i = \sum_{j=1}^{4} (a_{ij})^{-1} \Delta T_{\lambda j}/l \quad (2)$$

where $a_{ij}$ is an absorption coefficient of each component i ($HbO_2$, Hb, $CyO_2$, Cy) for each wavelength $\lambda_j$ ($\lambda_1$, $\lambda_2$, $\lambda_3$, $\lambda_4$) and is predetermined from FIGS. 4(a) and (b), and l is the length of the patient's head 40 along the travelling direction of the near infrared light.

As the above-detected density variation components, $\Delta X_{HbO2}$, $\Delta X_{Hb}$, $\Delta X_{CyO2}$ and $\Delta X_{Cy}$, reflect the variation of oxygen quantity in the brain, the variation of oxygen quantity in the brain can be determined by outputting these detected results from the output device 64. The diagnosis thus is made based on these results.

To accurately perform the examination it is necessary for the illumination-side fixture 51 and the detection-side fixture 53 to be firmly fitted to the prescribed position of the head 40. When the fitting condition of the illumination-side fixture 51 or the detection-side fixture 52 is changed, the illumination quantity to the head 40 or transmission quantity from it is changed even if the output quantities of near infrared light rays emitted from the respective light sources LD1 to LD4 are kept constant. Therefore the variation of the oxygenation cannot be correctly measured.

To prevent the above problem, the conventional examination apparatus has a function to watch whether the fitting position of the detection-side fixture is changed or not by detecting the dark light by the transmission light detection device 54 in the phase $\phi n1$ of the cycle CYn.

While this conventional examination apparatus can detect the change of fitting position of the detection-side fixture 52, it cannot detect the change of fitting position of the illumination-side fixture 51. Therefore, the conventional apparatus cannot sense the variation of the transmission quantity detected by the transmission light detection device 54 which has been caused by the variation of the illumination light quantity to the head 40 originating from the change of the fitting position of the illumination-side fixture 51. Thus the conventional apparatus fails to correctly measure the cerebral oxygenation. Moreover, the conventional apparatus cannot sense the dangerous situation in which the near infrared light rays from the light sources LD1 to LD4 illuminate one's eye when the fitting position of the illumination-side fixture 51 is changed.

SUMMARY OF THE INVENTION

Therefore, an object of the present invention is to provide an examination apparatus that detects the change of the fitting position of the illumination-side fixture and correctly measures the oxygenation, and at the same time, assures that safety is taken into consideration.

An examination apparatus of the present invention comprises: light source means which emits plural electromagnetic waves with different wavelengths; an illumination-side fixture which illuminates a measuring object by the electromaganetic waves emitted from the light source means and introduces reflected electromagnetic waves from the measuring object to fitting position detection means; and a detection-side fixture which introduces electromagnetic waves transmitted from the measuring object to transmission light detection means; wherein the fitting position detection means has reflection light detection means detecting reflection quantities of the reflected electromagnetic waves and output light detection means detecting output quantities from the light source means, and senses the change of the fitting position of the illumination-side fixture being based on the light quantities detected by the reflection light detection means and the output light detection means.

For example, the fitting position detection means calculates the variation of dark light quantity from the quantity at the beginning of measurement, in which the dark light is detected by the reflection light detection means when no electromagnetic wave is emitted from the light source means. And the fitting position detection means decides whether the variation of the dark light exceeds the prescribed tolerance limit or not. If it is decided that the tolerance limit is exceeded, regarding that the fitting position of the illumination-side fixture has been changed, for example, the operation of the examination apparatus is stopped or the alarm sound is generated.

Other and further objects, features and advantages of the invention will appear more fully from the following description taken in connection with the attached drawings.

BRIEF DESCRIPTION OF THE DRAWINGS

FIGS. 6(a) to (e) are time-charts of driving signals ACT1 to ACT4 and a control signal CTL, respectively.

DETAILED DESCRIPTION OF THE PREFERRED EMBODIMENTS

The embodiments of the present invention will be described in the following with referring to the attached drawings.

Figure 1:
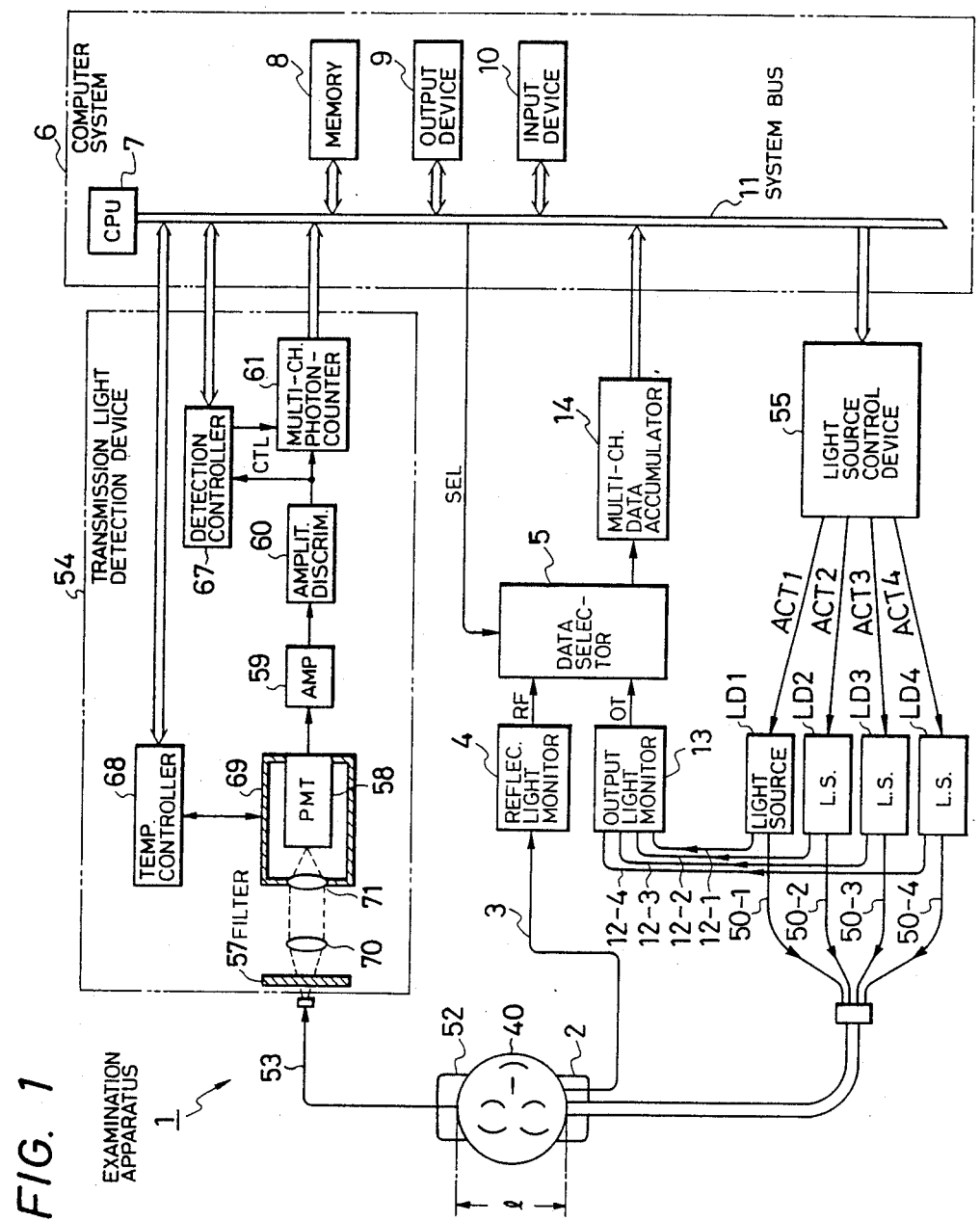
FIG. 1 is a system constitution of an examination apparatus which is an embodiment of the present invention.
Figure 5:
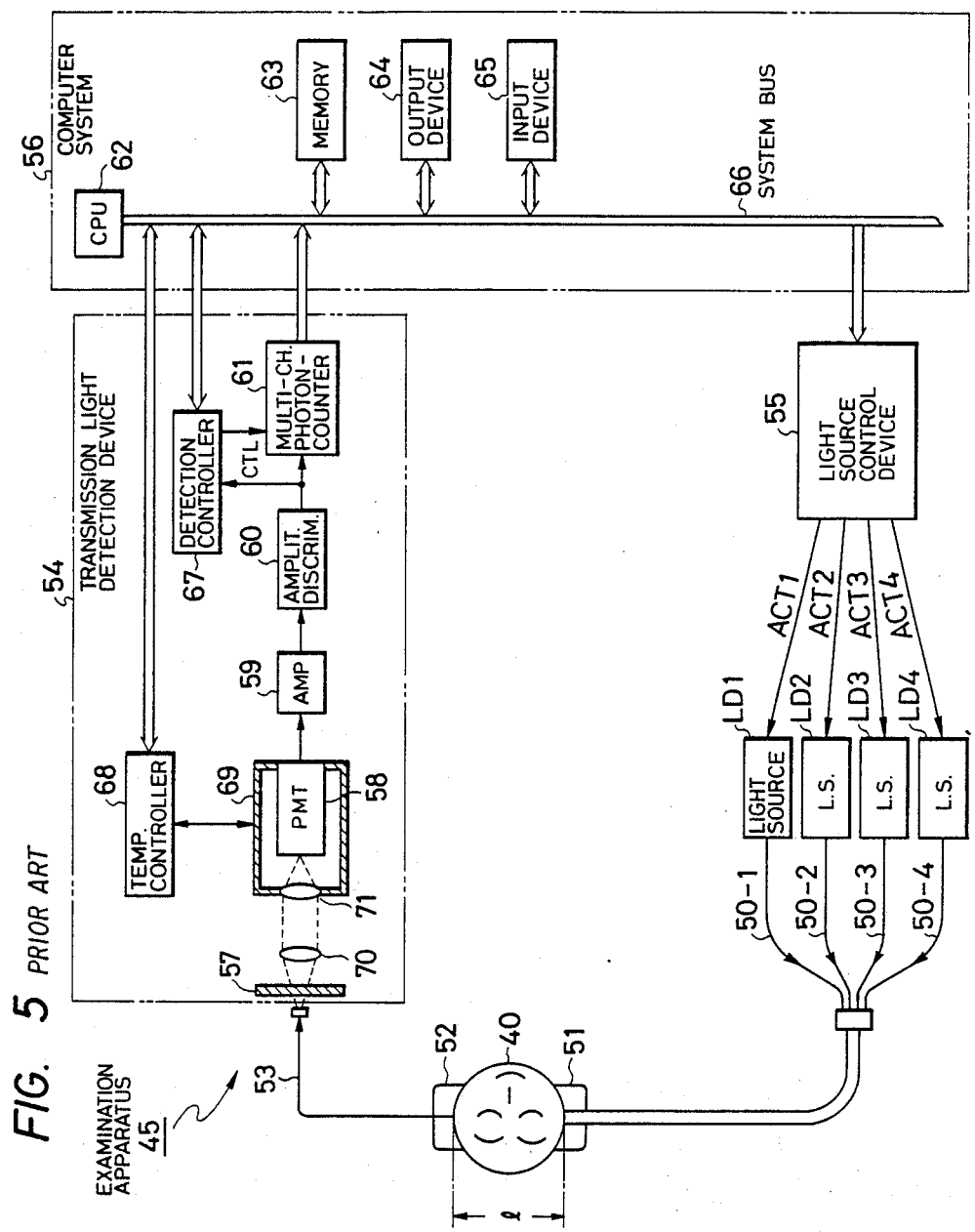
FIG. 5 is a system constitution of a conventional examination apparatus.

FIG. 1 shows a system constitution of an examination apparatus which is an embodiment of the present invention. In FIG. 1 the same reference numerals or characters are given to the blocks, parts or signals as those to the corresponding ones in FIG. 5 and the explanation for those will be omitted in the following description.

Not only the optical fibers 50-1 to 50-4 which introduce near infrared light rays emitted from the respective light sources LD1 to LD4 but also an optical fiber 3 which provides a reflection light monitor 4 with a reflected light from the head 40, are held by an illumination-side fixture 2 of an examination apparatus 1 shown in FIG. 1. And the near infrared light rays emitted from the light sources LD1 to LD4 are introduced to an output light monitor 13 by optical fibers 12-1 to 12-4, respectively.

For example, the reflection light monitor 4 and the output light monitor 13 consist of photodiodes. These monitors convert the reflected light and the output light into analog electric signals and output those as a reflection signal RF and an output signal OT, respectively. The reflection signal RF from the reflection light monitor 4 and the output signal OT from the output light monitor 13 are sent to a data selector 5. The reflection signal RF or output signal OT is selected in the data selector 5 according to a selection signal SEL sent from a computer system 6, A/D-converted and sent to a multi-channel data accumulator 14.

As same as the foregoing computer system 56, the computer system 6 comprises a processor 7, a memory 8, an output device 9, an input device 10 and a system bus 11 which connects these devices each other. Furthermore, the computer system 6 has a function to watch the change of the fitting position of the illumination-side fixture 2.

While the examination apparatus 1 with this constitution can detect the change of the fitting position of the detection-side fixture 52 by the transmission light detection device 54 and the computer system 6, which is the same function as the one with the conventional examination apparatus, it can also detect the change of the fitting position of the illumination-side fixture 2 by the reflection light monitor 4, the output light monitor 13, the data selector 5, the multi-channel data accumulator 14 and the computer system 6.

Figure 2:
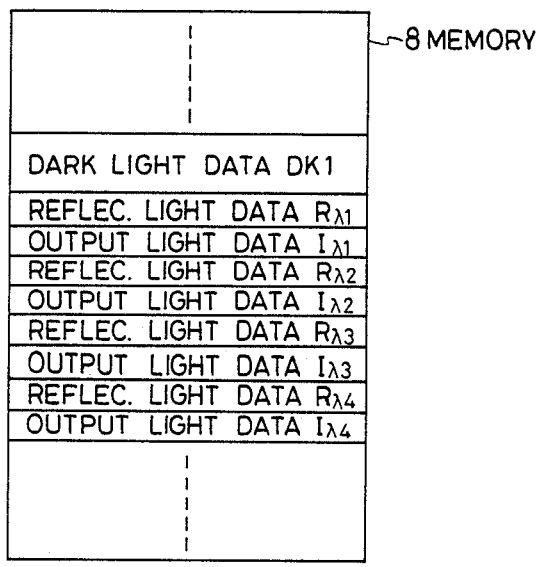
FIG. 2 shows data in a memory of a computer system of the examination apparatus shown in FIG. 1.

When the instruction of the start of examination is given from the input means 10, e.g. a keyboard, the light source control device 55 derives the light sources LD1 to LD4 through the driving signals ACT1 to ACT4 as shown in FIGS. 6(a) to (d), respectively. At the phase $\phi n1$ in the cycle CYn no near infrared light is emitted from the light sources LD1 to LD4 and the reflection light monitor 4 detects the dark light from the head 40 through the optical fiber 3. The detected dark light is in turn converted into an analog electric signal by the reflection light monitor 4, selected and converted into a digital signal of 12 bits by the data selector 5, and sent to the multi-channel data accumulator 14. The multi-channel data accumulator 14 accumulates the received digital signal of 12 bits (dark light signal) over one measurement period $M_k$ and sends an accumulation result DK1 to the computer system 6. The computer system 6 stores the received accumulation result DK1 of the dark light data in the memory 8 in such a manner as shown in FIG. 2.

In the next phase $\phi n2$ in the cycle CYn the light source LD1 is driven and the near infrared light is emitted from the light source LD1. The reflection light monitor 4 detects the reflection light from the head 40 through the optical fiber 3 and the output light monitor 13 detects the output light from the light source LD1. In the same procedure as in the dark light detection, the reflection light from the optical fiber 3 and the output light from the light source LD1 are converted into analog electric signals by the reflection light monitor 4 and the output light monitor 13, respectively, and sent to the multi-channel data accumulator 14 through the data selector 5. The multi-channel data accumulator 14 accumulates each of the two digital signals over one measuring period $M_k$. Therefore, in the phase $\phi n2$ the reflection light data $R_{\lambda 1}$ and the output light data $I_{\lambda 1}$ are sent to the computer system 6 when the measurement over one measuring period $M_k$ is finished. The computer system 6 stores these data in the memory 8 in such a manner as shown in FIG. 2 through the system bus 11.

In the next phases $\phi n3$, $\phi n4$ and $\phi n5$ in the cycle CYn, the light sources LD2, LD3 and LD4 are sequentially driven and the respective reflection light data $R_{\lambda 2}$, $R_{\lambda 3}$, $R_{\lambda 4}$ and the output light data $I_{\lambda 2}$, $I_{\lambda 3}$ and $I_{\lambda 4}$ are obtained in the same procedure as in the phase $\phi n2$. These data are stored in the memory 8 of the computer system 6 in such a manner as shown in FIG. 2. Though in the foregoing description the reflection light data are detected for all of wavelengths $\lambda_1$ to $\lambda_4$, it is not always necessary for the reflection light data to be detected for all of wavelengths, that is, the reflection light data may be detected for at least one wavelength. It should be noted that at the same time as the foregoing detections of the reflection light data $R_{\lambda 1}$ to $R_{\lambda 4}$ and the output light data $I_{\lambda 1}$ to $I_{\lambda 4}$, the dark light data D and the transmission light data $T_{\lambda 1}$ to $T_{\lambda 4}$ are detected by the transmission light detection device 54 and stored in the memory in the same manner as in the conventional examination apparatus 45.

Based on the dark light data DK1, the reflection light data $R_{\lambda 1}$ to $R_{\lambda 4}$ and the output light data $I_{\lambda 1}$ to $I_{\lambda 4}$ which have been detected over one measuring period $M_k$, reflectivities $\delta_1$, $\delta_2$, $\delta_3$ and $\delta_4$ are calculated as:

$$\delta_i = R_{\lambda i}/I_{\lambda i} \; (i=1 \text{ to } 4). \quad (3)$$

Instead of the above equation, the following definition may be adopted:

$$\delta_i = (R_{\lambda i} - DK1)/I_{\lambda i} \; (i=1 \text{ to } 4) \quad (4)$$

where $R_{\lambda i}$ in equation (3) is replaced by $(R_{\lambda i} - DK1)$.

Using the reflectivities $\delta_1$, $\delta_2$, $\delta_3$ and $\delta_4$ calculated from the equation (3) or (4) and the corresponding reflectivities obtained at the start of measurement $M_o$, the processor 7 determines variations of reflectivities $\Delta\delta_1$, $\Delta\delta_2$, $\Delta\delta_3$ and $\Delta\delta_4$. If one of the variations of reflectivities $\Delta\delta_1$, $\Delta\delta_2$, $\Delta\delta_3$ and $\Delta\delta_4$ or the variation of the dark light data $\Delta\epsilon$ is larger than the respective predetermined threshold values, the indication is that the fitting position of the illumination-side fixture to the head 40 has been changed and the illumination angle to the outer skin layer of the head 40 and the reflectivity of it have been varied beyond the respective prescribed ranges. The computer system 6 makes the output device 9 display some message to warn of the abnormality or to generate an alarm sound. Moreover, the computer system 6 makes the light sources LD1 to LD4 stop their operations so as not to emit near infrared light rays, thereby assuring the object person's safety.

The foregoing embodiment of the examination apparatus senses not only the change of fitting position of the detection-side fixture 52 as same as the conventional apparatus, but also senses the change of fitting position of the illumination-side fixture 2 as the variation of the reflectivity or the dark light. Therefore, the foregoing embodiment of the examination apparatus can measure the oxygenation of body organs more reliably and assure the safety of the object person even if the fitting position of the illumination-side fixture is changed.

Though the near infrared light rays with four different wavelength $\lambda_1$ to $\lambda_4$ are used in the foregoing embodiment, the number of wavelengths is not limited to four, that is, the number may be two and other light sources emitting near infrared light rays with wavelengths other than $\lambda_1$ to $\lambda_4$ may be added. Moreover, the near infrared light rays with different wavelengths may be obtained by using one white light source and filtering the white light emitted from it. And the electromagnetic wave emitted from the light source is not limited to near infrared light, that is, far infrared light, visible light, microwave, etc. may be used.

Figure 3:
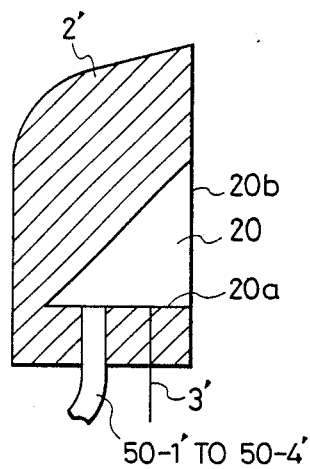
FIG. 3 is a sectional view illustrating an example of a modified illumination-side fixture.
Figure 4A:
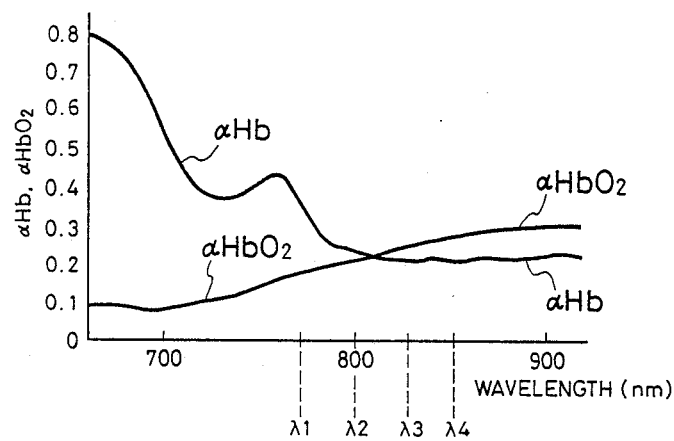
FIGS. 4(a) and (b) are graphs of absorption spectra of hemoglobin and cytochrome, respectively.
Figure 4B:
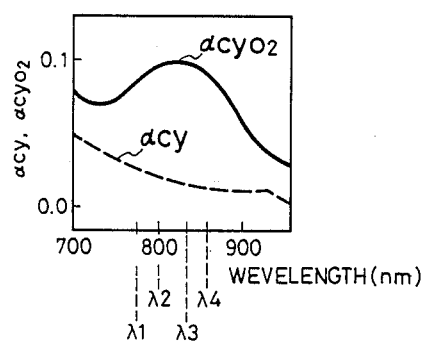

In the illumination-side fixture 2 shown in FIG. 1, ends of the optical fibers 50-1 to 50-4 introducing emitted light rays and end of the optical fiber 3 introducing reflected light rays are directly opposed to the head 40. Instead of the fixture 2 the illumination-side fixture 2' with another structure shown in FIG. 3 may be used. The illumination-side fixture 2' has a prism 20. One surface 20b of the prism 20 is applied to the head 40 and the emitted light rays are introduced by the optical fibers 50-1' to 50-4' so as to be made incident on the other surface 20a of the prism 20. The reflected light from the head 40 is received by the end of the optical fiber 3' on the surface 20a. The size of the illumination-side fixture 2' can be made small compared with that of the fixture 2. And in the fixture 2', the optical fibers 50-1' to 50-4' and 3' can be installed along the head 40. Therefore, even when the head 40 somewhat moves, the fitting position of the fixture 2' does not change much, resulting in more reliable and safer measurement. Moreover, the detection-side fixture may also employ the structure as shown in FIG. 3.

The application of the examination apparatus according to the present invention is not limited to the medical field but covers many fields including mere measurements. And measuring objects are not limited to the body organs but may be general ones such as a piece of flesh.

What is claimed is:

1. An examination apparatus for measuring the oxygenation in an object with electromagnetic wave transmission spectrophotometry, comprising:
   light source means for sequentially emitting electromagnetic waves with different wavelengths;
   an illumination-side fixture for making said electromagnetic waves introduced from said light source means incident on a measuring object and detecting reflected electromagnetic waves from said measuring object;
   reflection light detection means for detecting said reflected electromagnetic waves introduced from said illumination-side fixture and outputting reflection light data;
   output light detection means for detecting emitted electromagnetic waves from said light source means and outputting output light data; and
   a computer system for receiving said reflection light data from said reflection light detection means and output light data from said output light detection means, and judging whether a fitting position of said illumination-side fixture has been changed on the basis of said reflection light data and said output light data.

2. An examination apparatus as claimed in claim 1, wherein said electromagnetic waves are near infrared light rays.

3. An examination apparatus as claimed in claim 1, wherein
   said reflection light detection means further detects dark light reflected from said measuring object when said electro-magnetic waves are not emitted from said light source means and outputs dark light data; and
   said computer system receives said dark light data from said reflection light detection means, calculates variations of said dark light data from said dark light data at a beginning of a measurement period, and judges whether said fitting position has been changed on the basis of said variations of said dark light data.

4. An examination apparatus as claimed in claim 1, wherein
   said computer system calculates reflectivities which are defined as ratios of said reflection light data to said respective output light data, calculates variations of said reflectivities from said ratios at a beginning of a measurement period, and judges whether said fitting position has been changed on the basis of said variations of said calculated reflectivities.

5. An examination apparatus as claimed in claim 1, wherein
   said reflection light detection means further detects dark light reflected from said measuring object when said electro-magnetic waves are not emitted from said light source means and outputs dark light data; and
   said computer system calculates differences between said reflection light data and said dark light data, and reflectivities which are defined as ratios of said calculated differences to said respective output light data, calculates variations of said reflectivities from said ratios at a beginning of a measurement period, and judges whether said fitting position has been changed on the basis of said variations of said reflectivities.

6. An examination apparatus as claimed in claim 1, wherein said reflection light detection means and said output light detection means comprise:
   a reflection light monitor detecting said reflected electro-magnetic wave and converting said reflected electro-magnetic wave into an analog electric signal of reflection light;
   an output light monitor detecting said emitted electro-magnetic wave and converting said emitted electro-magnetic wave into an analog electric signal of output light;
   a common data selector receiving said analog electric signals of reflection light and output light, selecting between said analog electric signals according to a selection signal sent from said computer system, and converting selected analog electric signals into digital signals; and
   a common multi-channel data accumulator receiving said digital signals, accumulating received digital signals over a prescribed measurement period at every wavelength of emitted electromagnetic waves, and outputting accumulated digital signals as either said reflection light data or said output light data.

* * * * *